United States Patent [19]

Albrecht et al.

[11] Patent Number: 5,935,082

[45] Date of Patent: *Aug. 10, 1999

[54] ASSESSING CARDIAC ELECTRICAL STABILITY

[75] Inventors: Paul Albrecht, Bedford; Jeffrey M. Arnold, Wellesley; Richard J. Cohen, Waban, all of Mass.

[73] Assignee: Cambridge Heart, Inc., Bedford, Mass.

[*] Notice: This patent is subject to a terminal disclaimer.

[21] Appl. No.: 08/856,990

[22] Filed: May 15, 1997

Related U.S. Application Data

[63] Continuation-in-part of application No. 08/379,375, Jan. 26, 1995, Pat. No. 5,713,367, and application No. 08/557,883, Nov. 14, 1995, Pat. No. 5,704,365
[60] Provisional application No. 60/017,655, May 15, 1996.
[51] Int. Cl.$^6$ ................................................. A61B 5/0452
[52] U.S. Cl. ................................................................ 600/515
[58] Field of Search ........................... 600/509, 511–513, 600/546, 547, 901

[56] References Cited

U.S. PATENT DOCUMENTS

| | | |
|---|---|---|
| 4,082,087 | 4/1978 | Howson . |
| 4,458,691 | 7/1984 | Netravali . |
| 4,458,692 | 7/1984 | Simson . |
| 4,630,204 | 12/1986 | Mortara . |
| 4,732,157 | 3/1988 | Kaplan et al. . |

(List continued on next page.)

OTHER PUBLICATIONS

Adam et al., "Ventricular Fibrillation and Fluctations in the Magnitude of the Repolarization Vector," Computers in Cardiology, pp. 241–244 (1982).

Adam et al., "Fluctuations in T-Wave Morphology and Susceptibility to Ventricular Fibrillation," J. Electrocardiology 17(3), pp. 209–218 (1984).

Adam et al., "Estimation of Ventricular Vulnerability to Fibrillation Through T-Wave Time Series Analysis," Computers in Cardiology, pp. 307–310 (1981).

El–Sherif et al., "Beat–to–Beat High–Resolution Electrocardiogram; Technical and Clinical Aspects," Progress in Cardiovascular Diseases, vol. XXXV, No. 6, pp. 407–415 (1993).

El–Sherif et al., "Appraisal of a Low Noise Electrocardiogram," J. Am. Coll. Cardiol. 1(2), pp. 456–467 (1983).

Evans et al., "Redundancy Reduction for Improved Display and Analysis of Body Surface Potential Maps," Circulation Research, vol. 49, No. 1, pp. 197–203 (1981).

Kaufer et al., "Optimization of Multi–Ring Sensing Electrode Set," Annual International Conference of the IEEE Engineering in Medicine and Biology Society, vol. 12, No. 2, pp. 0612–0613 (1990).

Ring et al., "Exercise–Induced ST Segment Alternans," American Heart Journal, vol. 111, No. 5, pp. 1009–1111 (1986).

Smith et al., "Electrical Alternans and Cardiac Electrical Instability," Circulation, vol. 77, No. 1, 110–121 (1988).

Verrier et al., "Electrophysiologic Basis for T Wave Alternans as an Index of Vulnerability to Ventricular Fibrillation," J. of Cardiovascular Electrophysiology, vol. 5, No. 5, pp. 445–461 (1994).

*Primary Examiner*—Jeffrey R. Jastrzab
*Attorney, Agent, or Firm*—Fish & Richardson PC

[57] ABSTRACT

Cardiac electrical stability is assessed by generating a measure of cardiac electrical stability (e.g., an alternans measure) using a physiologic signal representative of activity of a patient's heart, generating a reference signal that provides information regarding whether the measure is representative of cardiac electrical stability, and visually presenting the measure and the reference signal in a way that permits visual evaluation of whether the measure is representative of cardiac electrical stability in view of characteristics of the reference signal.

31 Claims, 10 Drawing Sheets

U.S. PATENT DOCUMENTS

| | | |
|---|---|---|
| 4,802,491 | 2/1989 | Cohen et al. . |
| 4,974,598 | 12/1990 | John . |
| 4,979,110 | 12/1990 | Albrecht et al. . |
| 4,993,423 | 2/1991 | Stice . |
| 5,146,926 | 9/1992 | Cohen . |
| 5,148,812 | 9/1992 | Verrier et al. . |
| 5,188,116 | 2/1993 | Pommrehn et al. . |
| 5,234,404 | 8/1993 | Tuttle et al. . |
| 5,237,995 | 8/1993 | Cano . |
| 5,265,617 | 11/1993 | Verrier et al. . |
| 5,318,037 | 6/1994 | Evans et al. . |
| 5,323,783 | 6/1994 | Henkin et al. . |
| 5,341,811 | 8/1994 | Cano . |
| 5,348,020 | 9/1994 | Hutson . |
| 5,377,687 | 1/1995 | Evans et al. . |
| 5,421,342 | 6/1995 | Mortara . |
| 5,437,285 | 8/1995 | Verrier et al. . |
| 5,469,857 | 11/1995 | Laurent et al. . |
| 5,520,191 | 5/1996 | Karlsson et al. . |
| 5,520,683 | 5/1996 | Subramaniam et al. . |
| 5,560,370 | 10/1996 | Verrier et al. . |
| 5,570,696 | 11/1996 | Arnold et al. . |
| 5,713,367 | 2/1998 | Arnold et al. .......................... 128/704 |

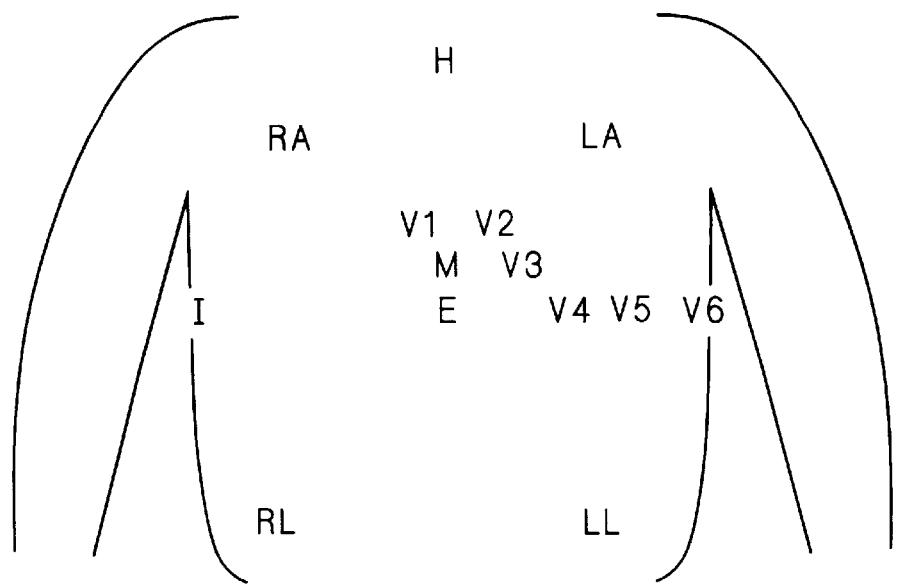

FIG. 3

| Electrode Name | Electrode Location | Type | Available Signals |
|---|---|---|---|
| RL | R. ILLIAC CREST | STANDARD | (DRIVEN GROUND) |
| RA | RIGHT SHOULDER | STANDARD | (REFERENCE) |
| LA | L. SHOULDER | STANDARD | LA |
| LL(F) | L. ILLIAC CREST | MULTIPLE | LLa, LLb, LLc, LLi |
| V1 | V1 | STANDARD | V1 |
| V2 | V2 | STANDARD | V2 |
| V3 | V3 | STANDARD | V3 |
| V4(C) | V4 | MULTIPLE | V4, V4a, V4i |
| V5 | V5 | STANDARD | V5 |
| V6(A) | V6 | MULTIPLE | V6, V6a, V6b, V6i |
| I | R. V6 POSITION | MULTIPLE | I, Ia, Ib, Ii |
| H | BELOW NECK | MULTIPLE | H, Ha, Hi |
| E | BETWEEN A & I | MULTIPLE | E, Ea, Ei |
| M | BACK | MULTIPLE | M, Ma, Mb, Mi |

| Row | Signal | Row | Signal |
|---|---|---|---|
| 1 | LA | 17 | V6i |
| 2 | LL | 18 | I |
| 3 | LLa | 19 | Ia |
| 4 | LLb | 20 | Ib |
| 5 | LLc | 21 | Ii |
| 6 | LLi | 22 | H |
| 7 | V1 | 23 | Ha |
| 8 | V2 | 24 | Hi |
| 9 | V3 | 25 | E |
| 10 | V4 | 26 | Ea |
| 11 | V4a | 27 | Ei |
| 12 | V4i | 28 | M |
| 13 | V5 | 29 | Ma |
| 14 | V6 | 30 | Mb |
| 15 | V6a | 31 | Mi |
| 16 | V6b | 32 | Resp |

FIG. 7

ALTERNANS VECTOR SPECTRUM REPORT

CAMBRIDGE HEART, INC.
BEDFORD, MA 01730

PATIENT INFORMATION

| Patient | : | | | | Date : 10-Oct-95 |
|---|---|---|---|---|---|
| ID | : Example 1 | | | | Time : 06:52 |
| Height | : 182 cm | Age | :65 | Medications : ACE-Inhib. | |
| Weight | : 72 kg | Sex | :M | : | |
| Physician | : | | | | |
| Technician | : | | | | |

TEST DETAIL

| Protocol | : ACES-25 | Test Time | : 12:04 min | HR | : 108 BPM | # Beats | : 128 | Noise | : 0.59 uV |
|---|---|---|---|---|---|---|---|---|---|
| Stage | : 2 | Stage Time | : 0:54 | RPM | : | % Bad | : 1.6% | | |

TEST RESULTS

Max Valt of 7.59 in lead eV4 with ratio 18.59

|  | eVM | eX | eY | eZ | eV4 |
|---|---|---|---|---|---|
| V alt (uV) | 1.35 | 2.60 | 0.55 | 2.58 | 7.59 |
| Ratio | 14.21 | 42.39 | 1.27 | 37.67 | 18.59 |
| Noise (uV) | 0.59 | 0.55 | 0.71 | 0.50 | 1.90 |
| Std (uV) | 0.36 | 0.40 | 0.48 | 0.42 | 1.76 |

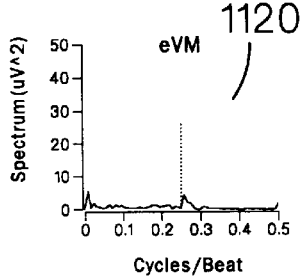 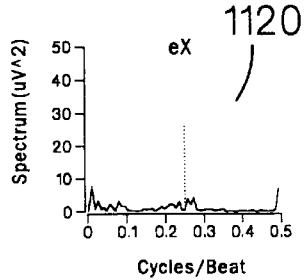 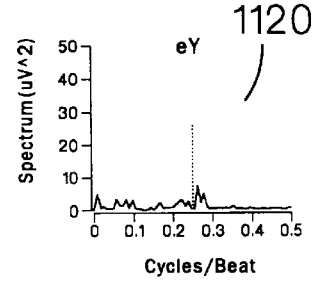
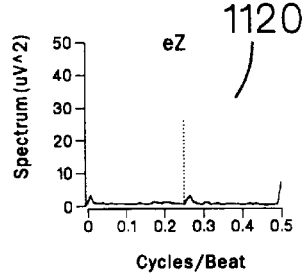 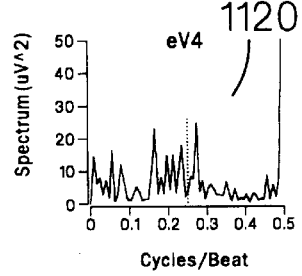 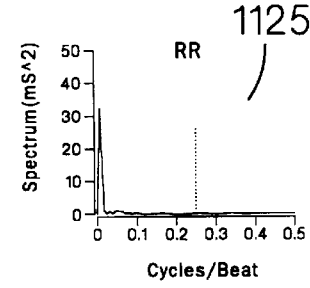

FIG. 11

ASSESSING CARDIAC ELECTRICAL STABILITY

CROSS REFERENCE TO RELATED APPLICATIONS

This application claims the benefit of U.S. Provisional Application No. 60/017,655, filed May 15, 1996 and entitled "Assessing Cardiac Electrical Stability". This application also is a continuation-in-part of U.S. application Ser. No. 08/379,375, now U.S Pat. No. 5,713, 367, filed Jan. 26, 1995 and entitled "Measuring and Assessing Cardiac Electrical Stability", and U.S. application Ser. No. 08/557,883, now U.S. Pat. No. 5,704,365 filed Nov. 14, 1995 and entitled "Using Related Signals to Reduce ECG Noise", both of which are incorporated herein by reference.

BACKGROUND OF THE INVENTION

The invention relates to assessing cardiac electrical stability.

Sudden cardiac death may result from disturbances of electrical conduction in the heart. A great majority of sudden cardiac deaths result from ventricular fibrillation, a disorganized pattern of electrical activity in the ventricles of the heart that leads to a disorganized pattern of mechanical contraction and results in the cessation of effective pumping action. Another disturbance of heart conduction processes, ventricular tachycardia, also reduces the effectiveness of the pumping action of the heart. Ventricular tachycardia can degenerate into ventricular fibrillation.

Sudden cardiac death may be prevented by identifying individuals at risk. It has been determined that alternans, a subtle beat-to-beat change in the repeating pattern of an electrocardiogram (ECG) waveform, can be indicative of electrical instability of the heart and increased susceptibility to sudden cardiac death. Alternans is an ABABAB . . . pattern of variation of waveform shape between successive beats in an ECG waveform. The level of alternans characterizes an individual's cardiac electrical stability.

The physiologic signal underlying an ECG waveform may be obtained through electrodes attached to a patient's chest. Typically, the electrodes include an electrically conductive gel that contacts the patient's skin and detects electrical signals produced by the patient's heart. The detected signals are then transmitted to ECG circuitry for processing and display.

SUMMARY OF THE INVENTION

The invention is directed to assessing cardiac electrical stability by presenting measurements of cardiac electrical stability (e.g., alternans measures) in conjunction with reference signals indicative of factors that are important for the interpretation of the measurements and that may affect whether those measurements are representative of actual cardiac electrical instability. When measurements such as alternans measurements are presented together with reference signals in this manner, physicians or other qualified medical personnel may evaluate whether a level of alternans occurring at a particular time is indicative of cardiac instability or, instead, is indicative of other factors such as interfering noise. This enables the physician to diagnose the patient's cardiac electrical stability with a high degree of confidence in the accuracy of the diagnosis.

In general, three types of reference signals are useful in determining whether alternans measurements are representative of actual alternans. The first type of reference signal identifies processes that may mask or mimic the presence of alternans and interfere with the measurement of alternans. For example, if a patient is exercising at one half of the heart rate, noise induced by the exercise may result in a false indication that alternans is present. The second type of reference signal provides an indication of factors that may influence the generation of alternans. For example, it has been found that alternans is substantially less likely to occur when a patient's heart rate is at a low level. Thus, display of the heart rate in conjunction with the alternans measure lets the physician evaluate whether an extended period in which no alternans is detected is indicative of cardiac stability of the patient or of an insufficient heart rate. The third type of reference signal provides useful auxiliary information. For example, it has been found that alternans in the presence of myocardial ischemia (i.e., reduced myocardial blood flow) is a strong indicator of cardiac electrical instability. For this reason, a reference signal indicative of the presence of ischemia provides information useful in evaluating whether an alternans measure is indicative of cardiac electrical instability.

One reference signal that has been found to be particularly useful in evaluating whether an alternans measure is representative of actual alternans is a measure of the frequency content of the patient's respiratory activity. Rather than just indicating the rate of respiratory activity at different points in time, the respiration reference signal indicates the degree to which the respiratory activity has frequency content that would be expected to interfere with or otherwise effect the alternans measurement. Displaying the respiration reference signal in conjunction with an alternans measurement permits a quick and accurate evaluation by the physician of the effects of respiration on the alternans measurement.

Other reference signals may provide measures of the heart rate and changes therein, or a measure of a rate of exercise or other physical activity. Reference signals may also indicate a degree to which bad or abnormal beats occur in the ECG waveforms from which the alternans measurements are determined, or a level of noise associated with the ECG waveforms.

In one aspect, generally, the invention features assessing cardiac electrical stability by generating an alternans measure using a physiologic signal representative of activity of a patient's heart, and generating a reference signal that provides information as to whether the alternans measure is representative of cardiac electrical stability. The alternans measure and the reference signal then are presented in a way that permits visual evaluation of whether the alternans measure is representative of cardiac electrical stability in view of characteristics of the reference signal.

Embodiments of the invention may include one or more of the following features. The alternans measure and the reference signal may be graphically displayed using, for example, a video display or a printer. The alternans measure and the reference signal may be displayed with respect to a common time axis. Portions of the common time axis may be marked. For example, the marked portions may correspond to time segments in which the alternans measure is expected to be more reliable than time segments to which unmarked portions of the common time axis correspond. Portions of the alternans measure may be shaded.

The reference signal may be indicative of a parameter that affects reliability of the alternans measure, such as a parameter that masks or mimics the presence of alternans. The reference signal also may be indicative of a parameter that affects generation of alternans.

The reference signal may be a measure of the patient's heart rate. For example, the reference signal may be a measure of mean or instantaneous values of the patient's heart rate at different times, or of variations in the patient's heart rate.

The reference signal may be a measure of defects in the physiologic signal. For example, when the physiologic signal is a sequence of ECG beats, the reference signal may be a measure of a number of ectopic beats in the sequence at different times.

The reference signal may be a measure of noise in the physiologic waveform. For example, the reference signal may be a measure of noise in a frequency band of the physiologic waveform. Bounds of the frequency band may vary over time and may be related to the patient's heart rate at different times. The reference signal also may be a measure of levels of noise in the physiologic waveform relative to amplitudes of the physiologic waveform at different times.

The reference signal may be a measure of the patient's respiratory activity, a measure of exercise by the patient, or a measure of the presence of ischemia. The reference signal also may be a measure of variations in ST segments of beats of an ECG signal. Similarly, the reference signal may be a measure of the QT segments of beats of an ECG signal, or of dispersion of those segments at different locations. A measure of QT dispersion may be generated by measuring the QT intervals for different ECG leads and comparing the QT intervals to generate the measure of QT dispersion.

In another aspect, generally, the invention features assessing cardiac electrical stability by generating a measurement of cardiac electrical stability (e.g., alternans or QT dispersion) using a physiologic signal representative of activity of a patient's heart, and generating a reference signal that provides information as to whether the measure is representative of cardiac electrical stability. The measure and the reference signal then are presented in a way that permits visual evaluation of whether the measure is representative in view of characteristics of the reference signal.

The invention also features systems and software for implementing the techniques described above. The techniques are not limited to any particular hardware or software configuration; they may find applicability in any computing or processing environment that may be used for assessing cardiac electrical stability. The techniques may be implemented in hardware or software, or a combination of the two. Preferably, the techniques are implemented in computer programs executing on programmable computers that each include a processor, a storage medium readable by the processor (including volatile and non-volatile memory and/or storage elements), at least one input device, and one or more output devices. Program code is applied to data entered using the input device to perform the functions described and to generate output information. The output information is applied to one or more output devices.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage medium or device (e.g., CD-ROM, hard disk or magnetic diskette) that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other features and advantages of the invention will become apparent from the following description, including the drawings, and from the claims.

DESCRIPTION OF THE DRAWINGS

FIG. 3 is a placement diagram for electrodes on a patient.

FIG. 4 is a table illustrating the location and type of the electrodes of FIG. 3 and defining the input signals that are recorded from those electrodes.

FIG. 7 is a table defining signal elements of a time series b(n).

FIGS. 9–12 illustrate reports produced by the system of FIG. 1.

DESCRIPTION OF THE PREFERRED EMBODIMENTS

Figure 1:
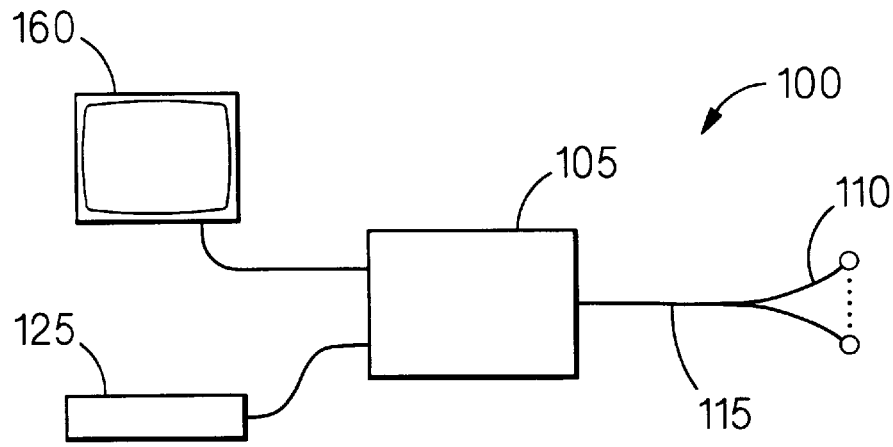
FIG. 1 is a block diagram of an ECG system.

FIG. 1 illustrates an electrocardiogram (ECG) system 100. The system includes a processor 105 and a set of electrodes 110. The electrodes 110 are attached to a patient's skin and positioned to detect ECG waveforms produced by the patient's heart as well as other signals. Each electrode 110 includes electrically conductive gel that contacts the patient's skin and conducts to the electrode any electrical signals that are present at the skin. Leads 115 connected between electrodes 110 and processor 105 provide the detected signals to processor 105.

Processor 105 analyzes the ECG waveforms to generate alternans measures and other signals. Processor 105 then presents the alternans measures and other signals to an operator of the system 100 by displaying them on a monitor 120 or by generating a printed representation of them using a printer 125.

Figure 2:
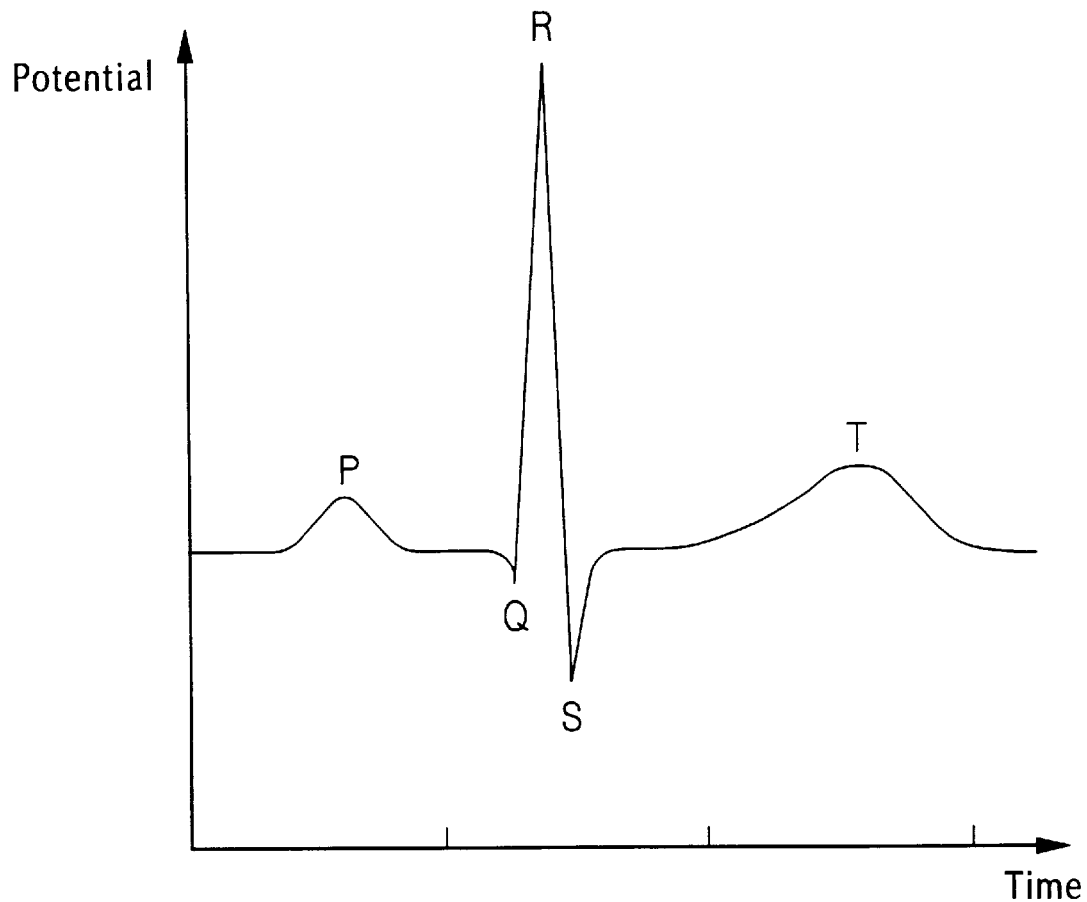
FIG. 2 is an ECG potential over a single beat.

Referring to FIG. 2, an ECG waveform for a single beat is typically referred to as a PQRST complex. The P wave appears at initiation of the beat and corresponds to activity in the atria, while the QRST complex follows the P wave and corresponds to ventricular activity. The QRS component represents the electrical activation of the ventricles, while the T wave represents their electrical recovery. The ST segment is a relatively quiescent period. In humans, it has been found that a level of variations in the T waves of successive beats is a good indicator of a patient's cardiac electrical stability. It also has been found that depression of the ST segment may occur during a bout of ischemia, and that T-wave alternans tends to occur in the presence of ischemia. Accordingly, the presence of a depression in the ST segment level may be indicative of whether an alternans measure is a representative measure.

The ECG signal produced by the patient's heart decreases as a function of the distance from the heart at which the ECG signal is measured. Accordingly, an ECG signal detected by an electrode 110 will vary from the actual ECG signal based on the placement of the electrode relative to the heart. An accurate approximation of the actual ECG signal may be generated by combining signals from multiple electrodes having known placement relative to the heart.

The ECG signal measured at the body surface may be represented by modelling the heart as a three-dimensional dipole source that produces an electrical signal which varies based on the distance from the heart in the X, Y and Z directions. Thus, the voltage detected by an electrode M that is located relative to the dipole at a coordinate given by the vector $(x_M, y_M, z_M)$ will be:

$$M(t)=x_M v_X(t)+y_M v_Y(t)+z_M v_Z(t).$$

Use of the dipole vector model of the heart has lead to the development of clinical systems that measure the X, Y and Z components of the dipole source through a linear combination of several electrodes. The most common known XYZ systems are the Frank lead system and the Bipolar system. In clinical practice, another common system of electrodes is the twelve lead system. The twelve lead system places greater emphasis on the electrodes on the left chest near the heart.

ECG system 100 includes fourteen electrodes 110 that are placed on the patient as illustrated in FIG. 3. This arrangement combines the electrodes of the Frank and standard 12 lead systems. The signals produced by the electrodes, along with their types, are illustrated in FIG. 4. Seven of the electrodes are conventional ECG electrodes having a single terminal (and producing a single signal), while the other seven electrodes are multi-segment electrodes having four terminals (and producing up to four signals).

Figure 5B:
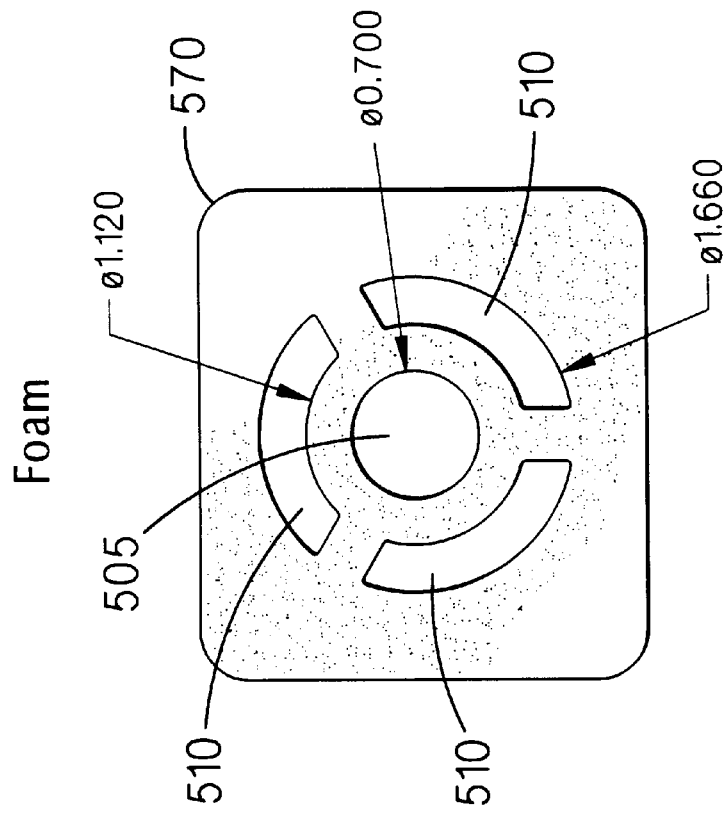
FIGS. 5A and 5B are diagrammatic views of components of a multi-segment electrode.
Figure 5A:
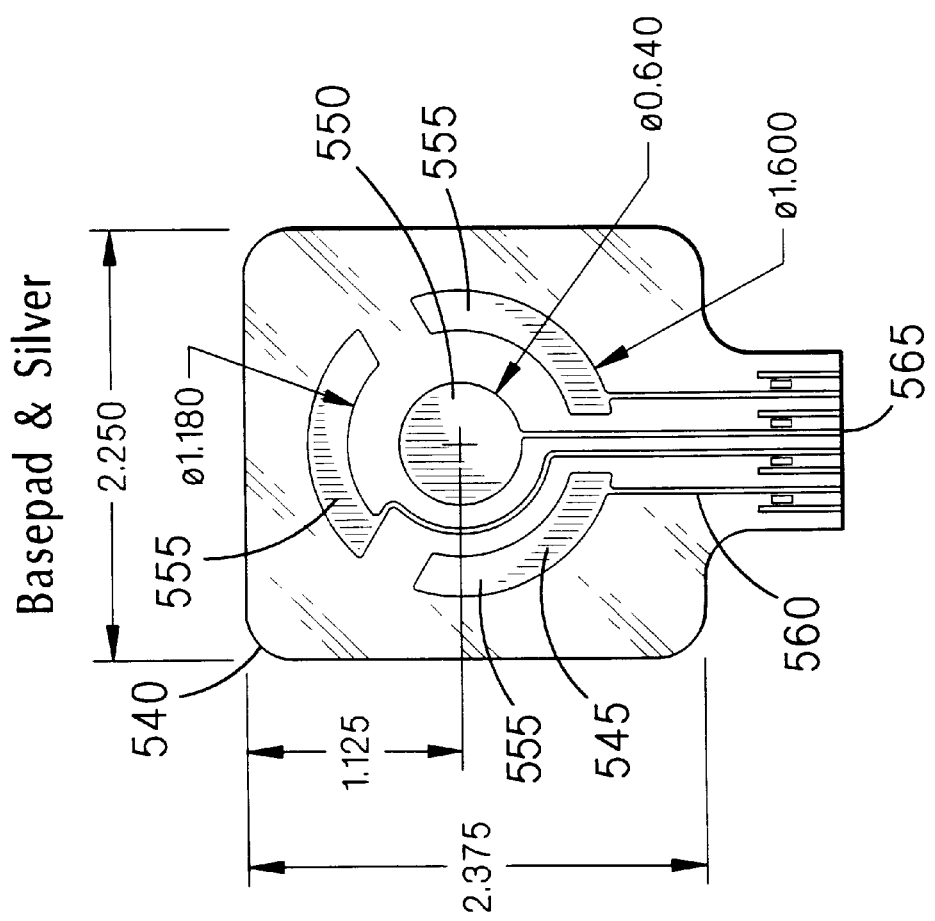

A multi-segment electrode is illustrated in FIGS. 5A and 5B. The multi-segment electrode is constructed from a film basepad 540 on which is printed silver-chloride ink 545. The ink is patterned to create a center segment 550 and annular segments 555 that provide electrical connection to the electrode gel. The ink pattern also creates traces 560 that continue to the bottom edge 565 of the basepad 540. At the bottom edge of the basepad 540, the traces are brought into a parallel configuration suitable for an edge connector.

A plastic flexible foam 570 is attached to the base pad 540. The foam includes cutout sections 505, 510 that correspond to the electrode segments 550, 555 and create wells that hold electrically conductive gel that makes an electrical connection from the ink to the skin. The surface of the foam is covered with an adhesive that adheres the electrode to the skin of the patient. The foam covers and insulates portions of the traces 560.

Multi-segment electrodes provide a number of advantages. First, an ECG signal and baseline noise will vary in different ways, if at all, between segments of the electrode. This is largely attributable to differences between the physical location of the heart and the locations of sources of noise. For example, when the heart is positioned relatively close to a multi-segment electrode and a noise source is positioned relatively far from the electrode, the ECG signal will vary to a greater degree from segment to segment than will the noise from the noise source. In addition, since the segments are all part of the same physical structure, the segments are affected similarly by movement due to respiration or other causes. Variations in noise due to patient movement can be adjusted between segments by introducing different DC bias currents at each segment of the electrode. Similar results could be obtained by using different electrolyte mixtures in the gel of each segment to vary the conductivity from segment to segment or by using different metal combinations on the foam basepad.

Processor 105 periodically samples the signals. When recording an ECG signal, processor 105 uses an isoelectric point of the signal as a zero voltage reference. Processor 105 measures the isoelectric point during the PQ interval between the P wave and QRS complex. The PQ interval is a good approximation to a zero ECG level because there is no major electrical activity in the heart at that time.

After acquiring the signals, the processor 105 processes the signals to produce an ECG waveform for further analysis or display. While an ECG waveform typically has a QRS amplitude measured in millivolts, an alternans pattern of variation with an amplitude on the order of a microvolt may be clinically significant. Accordingly, the processor 105 must produce the ECG waveform with extreme accuracy to permit effective detection of alternans. Achievement of this accuracy is complicated by the presence of noise in the electrode signals. The noise may result in beat-to-beat variations in the ECG waveform that have a larger magnitude than the alternans pattern of variation.

The noise in an ECG signal can be classified into three categories: baseline noise generated in the electrode, physiologic noise, and external electrical noise. The baseline noise is low frequency noise that appears as an undulating baseline upon which the ECG rides. Baseline noise is attributable to motion and deformation of an electrode and its associated gel. Baseline noise results from low frequency events such as patient respiration and patient motion. As a result, the magnitude of baseline noise tends to increase with exercise. However, it is during exercise that many important ECG measurements need to be made. Typically, the frequency content of baseline noise is below 10 Hz.

Physiologic noise results from other physiologic processes within the patient that interfere with the ECG signal. Skeletal muscle activity is the most common source of physiologic noise. The electrical activity of the skeletal muscles creates potentials that are additive with respect to the potentials created by the heart. The frequency content of the skeletal muscle signals is comparable to the frequency content of the QRS complex, and is typically greater than 10 Hz. When measuring T wave alternans, additional physiologic noise may result from changes in the position of the heart due to respiration or from changes in the projection of the electrical potential from the heart to the skin surface due to thoracic conductivity changes arising from the inflation and deflation of the lungs with respiration.

External electrical noise results, for example, from ambient electromagnetic activity near the system 100, electrode cable motion, and variations in amplifiers or other components of the ECG circuitry. External electrical noise may be eliminated or reduced through the use of high quality components and through the reduction of ambient electromagnetic activity by, for example, deactivating high power equipment.

Noise in the ECG waveform can easily mask the presence of alternans. The noise can also mimic the presence of alternans where there is none. For example, if a patient is breathing at one-half or one-third of the heart rate, the respiration may introduce a harmonic signal having the ABABAB . . . pattern of alternans. Similarly, motion that repeats with some periodicity, such as that resulting from exercise, can create electrode noise with a similar pattern. Furthermore, noise resulting from different sources, such as respiration and electrode noise, can interact and produce new periodicities, one of which may mimic alternans.

Noise can also adversely affect the measurement of other ECG parameters, such as the level of the ST segment. Baseline noise can interfere with measurement of the ST level of an ECG signal by misrepresenting the level of the ST segment. Clinically, a change in the ST level of greater than 0.1 millivolts (mV) is considered significant. The ST level is typically measured at 80 milliseconds beyond the end of the QRS complex and is measured relative to the isoelectric level determined from the PQ interval. Assuming that the PQ interval is approximately 200 milliseconds away from the ST segment point, a low frequency waveform that is changing at a rate of 0.5 mV per second can misrepresent the ST level by 0.1 mV (0.5 mV/second * 0.2 second). Muscle noise also can affect the ST level measurement. Muscle noise appears in bursts coordinated with muscle activity. Muscle noise increases with exercise and easily can be on the order of 0.1 mV RMS. For this reason, muscle noise can introduce a substantial error into the measurement of the ST level of any single ECG complex.

Similarly, baseline noise can interfere with the T wave alternans measurement because the frequency content of baseline noise often overlaps with the frequency content of T wave alternans. T wave alternans occurs at a frequency of every other beat. Thus, a heart rate of 60 beats per minute corresponds to an alternans repetition rate of 0.5 Hz. Since alternans is typically measured at heart rates between 60–120 beats per minute, the alternans rate is typically between 0.5 and 1 Hz. Baseline noise can have frequency components that occur at a frequency of every other beat, especially when the noise is driven by a periodic phenomenon such as respiration. When baseline noise occurs at a frequency of every other beat, it can mimic alternans. Typically, however, baseline noise is a broadband signal having a power spectrum that contains random levels of noise at different frequencies.

Processor 105 is configured to reduce the noise in the ECG waveforms before producing measures of alternans. Processor 105 achieves substantial reductions in the noise content of the beats of the ECG waveform by combining one or more ECG signals and one or more other signals in a way that causes the noise content of the signals to combine destructively while preserving the ECG content. The noise reduction techniques employed by processor 105 are discussed in detail in U.S. application Ser. No. 08/557,883, now U.S. Pat. No. 5,704,365 filed Nov. 14, 1995, and entitled "Using Related Signals to Reduce ECG Noise", which, as noted above, is incorporated herein by reference.

In general, processor 105 uses three techniques to reduce the noise content of the ECG waveform. First, processor 105 uses a technique referred to as electrode enhancement or electrode noise reduction. This technique uses an adaptive averaging of ECG signals from the multiple segments of a multi-segment electrode to reduce noise in a signal associated with the electrode. The technique also uses impedance measurements from the multi-segment electrodes to reduce baseline noise.

Next, processor 105 uses a technique referred to as lead optimization or vector enhancement to produce a set of signals for which processor 105 will generate alternans measurements. The vector enhancement technique uses signals produced by the electrode optimization technique as input signals and produces a set of five low-noise signals (VM, X, Y, Z and V4). VM is a vector magnitude defined as:

$$VM = \sqrt{X^2 + Y^2 + Z^2}$$

VM is immune to any alternans artifact created by rotation of the heart. The V4 signal is representative of the V1–V6 signals, which are known to contain information that is not present in the X, Y and Z signals. The V4 signal, which is produced by the electrode optimization technique, is not processed further using the vector enhancement technique.

Finally, processor 105 accounts for the effects of abnormal beats (also referred to as bad or ectopic beats). Abnormal beats are defined as beats that are more than 10% premature or that have a shape which differs from the shape of a normal beat by more than 10%. Beats preceding a premature beat are also treated as abnormal beats. Abnormal beats can add significantly to the noise level. Processor 105 may account for abnormal beats when preprocessing the electrode signals prior to performing electrode optimization, or may account for them when generating alternans measures.

Processor 105 may account for abnormal beats in a number of ways. In a first approach, processor 105 simply eliminates the abnormal beats from the sequence of beats. In another approach, processor 105 replaces an abnormal beat with a mean normal beat. In yet another approach, processor 105 separately analyzes each sequence of normal beats between abnormal beats and combines the analyses. Techniques for handling abnormal beats are discussed in U.S. application Ser. No. 08/379,375, filed Jan. 26, 1995 and entitled "Measuring and Assessing Cardiac Electrical Stability", which, as noted above, is incorporated herein by reference.

Figure 6:
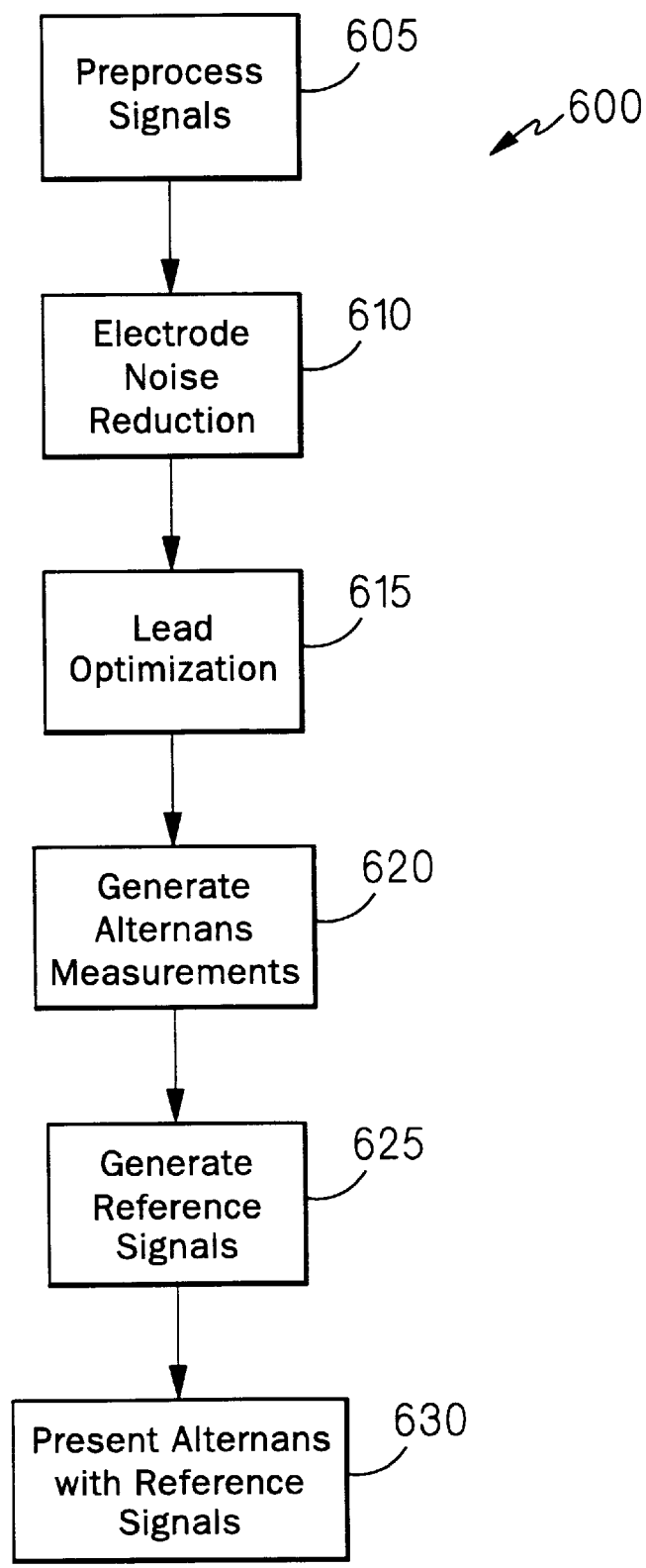
FIG. 6 is a flowchart of a procedure for producing alternans measures.

Processor 105 generates and presents alternans and related measures for a patient using the procedure 600 illustrated in FIG. 6. Initially, processor 105 preprocesses the signals produced by the electrodes 110 (step 605). This preprocessing includes amplifying and anti-alias filtering the signals, and digitizing the filtered signals at a sampling rate of 1 kHz to create a 32 row time series b(n).

Processor 105 obtains thirty two signals from the fourteen electrodes illustrated in FIG. 3. Each row of the time series corresponds to a signal from an electrode. The contents of each row is shown in FIG. 7. Of the thirty two signals, there are twenty four ECG signals, seven electrode impedance signals, and one respiratory/trans-thoracic impedance signal. The impedance signals are produced using a current injection technique.

The twenty four ECG signals are named after their corresponding electrodes. For multi-segment electrodes, the name of an electrode refers to the center electrode and the suffix "a", "b", or "c" refers to signals from the ring segments. For most of the multi-segment electrodes, two or three of the outer ring segments are joined together to form a larger segment. This reduces the number of ECG signals that need to be recorded. All of the ECG signals are recorded relative to the average of the voltages at the RA, LA and LL electrodes. This average is commonly referred to as the Wilson's central terminal.

The seven impedance signals measure the center segment impedances of the seven multi-segment electrodes. The impedance signals are named according to their corresponding electrode followed by the suffix "i".

The respiratory signal (Resp) is a measure of the impedance of the patient's chest from the right side to the left side. Because air does not conduct electricity as well as body tissues do, the impedance across the chest changes as the lungs inflate and deflate due to respiration. Respiration also introduces baseline noise due to expansion and compression of the electrodes and changes in the impedance between the heart and the body surface.

Processor 105 detects, aligns and classifies the beats within the time series b(n), and aligns each beat based on the QRS complex of the beat to produce beat matrices B(n).

Each beat matrix B(n) corresponds to a particular beat, with each row of the matrix corresponding to one of the input signals and each column of the matrix corresponding to the values of the signals at a particular point in time.

Next, processor 105 performs electrode noise-reduction (step 610) on the beat matrices B(n) to produce a set of twelve low-noise ECG signals (LA, LL, V1, V2, V3, V4, V5, V6, E, I, H and M). Processor uses these twelve signals as input signals for the vector enhancement technique (step 615). As noted above, processor 105 produces five low-noise signals (VM, X, Y, Z and V4) using the vector enhancement technique. In some instances, processor 105 may produce other combinations of low-noise ECG signals.

Processor 105 then generates alternans measurements for the low-noise ECG signals (step 620). Processor 105 measures the level of alternans ($P_{alt}$) as the power level of an ECG signal at 0.5 cycles/beat (referred to as $P_{0.5}$) minus the average power level in a noise reference band between 0.44 and 0.49 cycles/beat (referred to as $P_{noise}$):

$$P_{alt} = P_{0.5} - P_{noise}.$$

Alternans is considered significant when $P_{alt}$ is more than three times the standard deviation of $P_{noise}$.

Figure 8A:
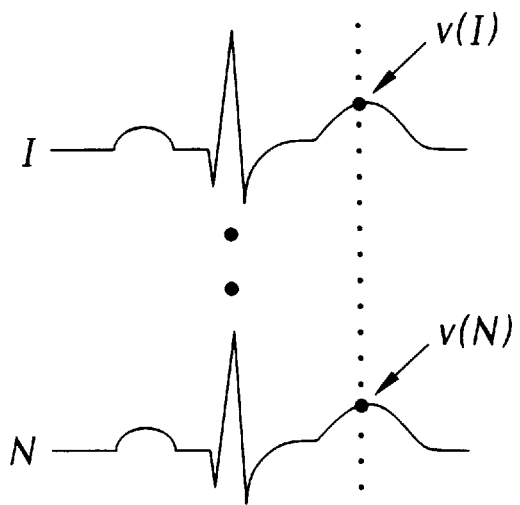
FIGS. 8A–8C are plots of physiologic signals over time.
Figure 8B:
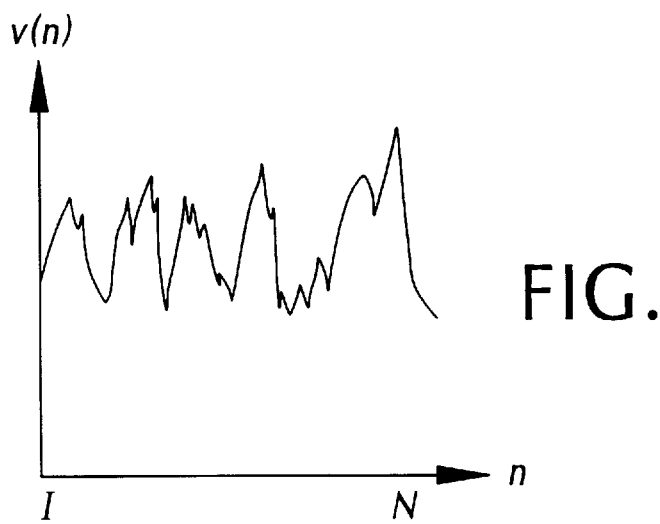
Figure 8C:
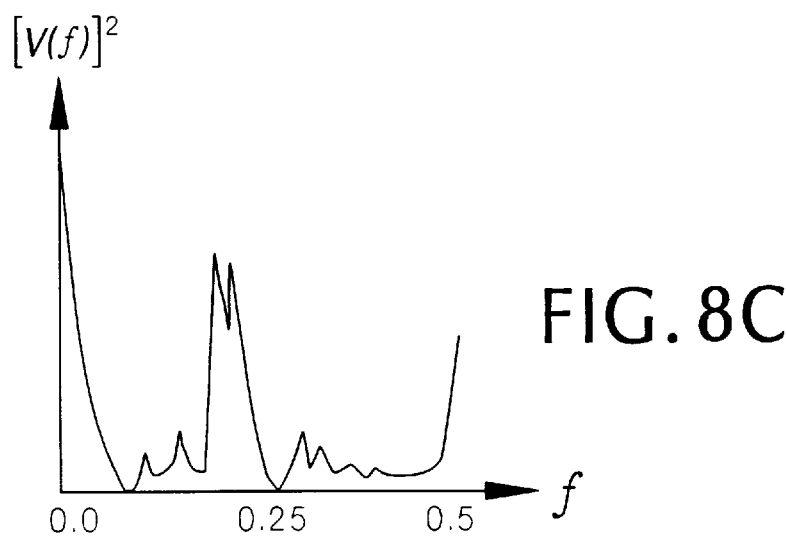

Processor 105 determines $P_{0.5}$ and $P_{noise}$ for each ECG signal of interest by performing a spectral analysis of the ECG signal. This analysis is illustrated in FIG. 8A–8C. First, as shown in FIG. 8A, processor 105 identifies a set of values 800 corresponding to the T-wave region of successive beats for a particular ECG signal. If values representative of a particular ECG signal for a series of beats were placed in a matrix, with each row of the matrix corresponding to a particular beat and each column of the matrix corresponding to a corresponding time within each beat, the set of values 800 would be the values in the column of the matrix corresponding to a point in the T-wave region of the beat. The set of values 800 may be represented as shown in FIG. 8B, where the vertical axis corresponds to the magnitude of the values and the horizontal axis corresponds to a beat number. Processor 105 then uses a FFT or other techniques to compute the power spectrum 805 (FIG. 8C) of the set of values in cycles per beat. In FIG. 8C, $P_{alt}$ is the value 810 of the power spectrum at 0.5 cycles per beat and $P_{noise}$ is the average of the values of the power spectrum in the region 815 from 0.44 to 0.49 cycles per beat.

Processor 105 generates an alternans voltage, $V_{alt}$, as the square root of $P_{alt}$:

$$V_{alt} = \sqrt{P_{0.5} - P_{noise}}.$$

Thus, for example, processor 105 generates an alternans voltage for the signal VM as:

$$V_{alt_{VM}} = \sqrt{P_{0.5_{VM}} - P_{noise_{VM}}}.$$

Processor 105 also generates an alternans ratio, k, as $P_{alt}$ divided by the standard deviation of $P_{noise}$:

$$k = \frac{(P_{0.5} - P_{noise})}{\sigma_{noise}}.$$

Next, processor 105 generates measures of a group of reference signals that represent factors that may affect the quality of the alternans measurements (step 625). The reference signals include measures of the heart rate, the relative number of bad or abnormal beats, the noise level, the exercise rate (when exercise is used to stimulate the heart), the respiratory activity, and variations in the heart rate.

Processor 105 may generate reference signals using techniques similar to those employed in generating alternans measures. For example, it has been found that respiration at a rate of 0.25 cycles/beat can result in an inaccurate alternans measurement because the second harmonic of that respiration rate is at the alternans frequency of 0.5 cycles per beat. Respiration may affect alternans measurements by inducing changes in the orientation of the heart, the shape of the thorax, and the conductivity of the lungs. Respiration also may induce baseline noise by moving the electrodes and may affect the RR interval (the interval between the R points of consecutive beats).

Processor 105 determines whether respiration includes a significant component at 0.25 cycles per beat by performing the power spectrum analysis discussed above on the respiration signal (Resp). Since the impact of respiration on the measurement of T-wave alternans is at issue, magnitudes of the respiration signal at times corresponding to the T-wave segments of successive beats are analyzed. After generating the power spectrum for the respiration signal, processor 105 normalizes the power spectrum to set the largest value of the spectrum equal to one. The level of respiration at 0.25 cycles/beat may then be expressed as $P_{0.25}$, the normalized power spectrum value at a frequency of 0.25 cycles/beat. In some instances, processor 105 may account for the sharpness of the peak at 0.25 cycles/beat by subtracting from $P_{0.25}$ values from the power spectrum at frequencies separated from 0.25 cycles/beat by a delta value:

$$P_{0.25}' = P_{0.25} - (P_{0.25-delta} + P_{0.25+delta})/2.$$

For example, if the delta value equals 0.05 cycles/beat, then processor 105 would generate $P_{0.25}'$ by subtracting one half of the sum of $P_{0.2}$ and $P_{0.3}$ from $P_{0.25}$.

Figure 9:
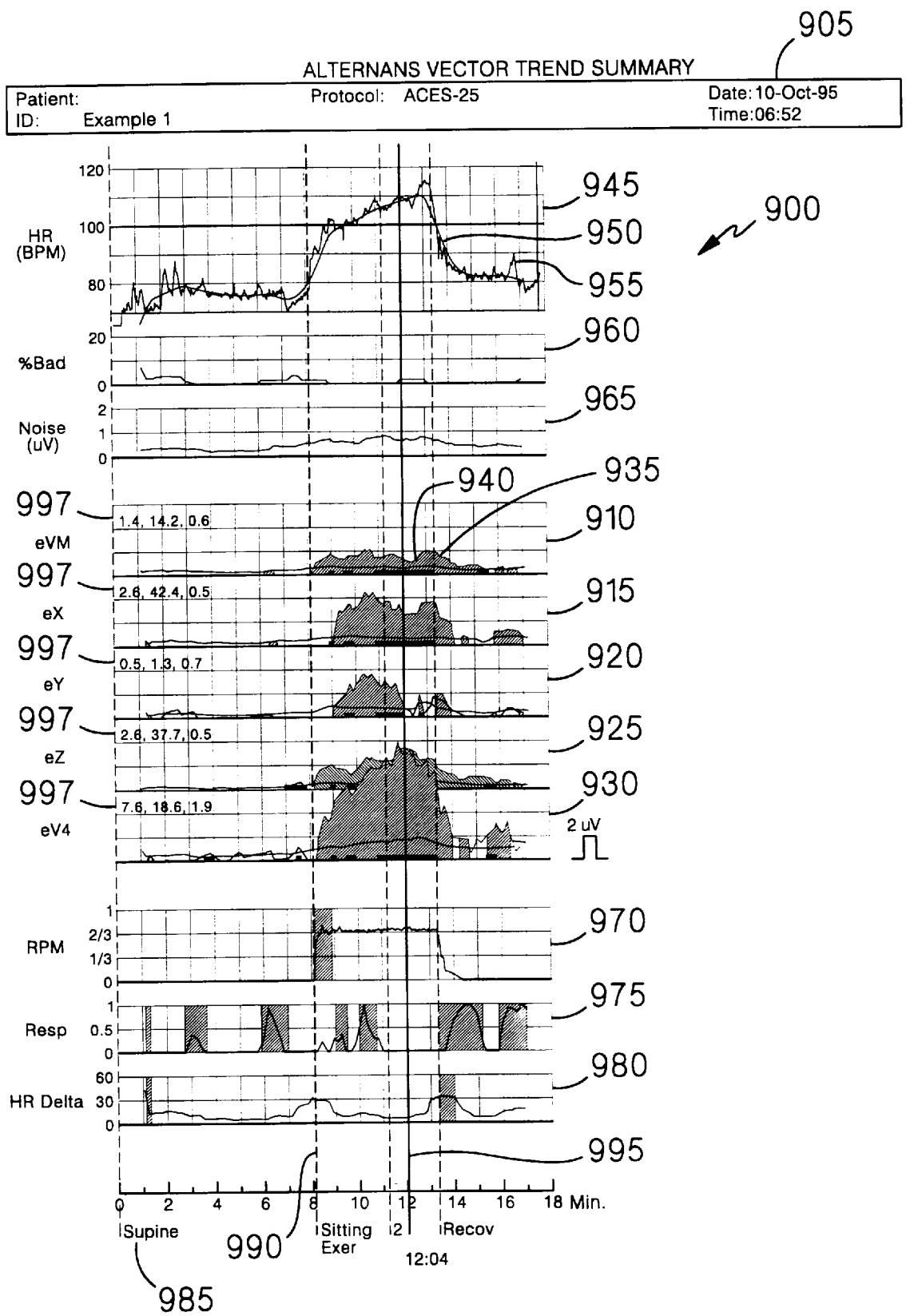

Finally, processor 105 presents the alternans measurements along with the reference signals in a way that permits visual evaluation of the degree to which the alternans measurements represent the actual presence of alternans (step 630). FIG. 9 illustrates a trend report 900 produced by processor 105. Report 900 may be displayed on the monitor 120 or produced in printed form by the printer 125. Report 900 also may be produced in other ways. For example, report 900 may be produced as an electronic file that is accessible at a later time to permit visual inspection of the alternans measurements relative to the reference signals at that time.

The report 900 includes an informational segment 905. This segment identifies the title of the report ("Alternans Vector Trend Summary"), the patient (by name and identification number), the testing/exercise protocol that resulted in the alternans measurements, and the date and time at which the measurements were produced.

Report 900 includes alternans measurements for the VM, X, Y, Z and V4 leads. These measurements are identified as eVM (910), eX (915), eY (920), eZ (925) and eV4 (930). The "e" preceding the name of each signal indicates that the signal has been enhanced using the noise reduction techniques noted above. The alternans measurements are displayed with respect to a grid having vertical sections that each correspond to 2 microvolts of alternans and horizontal sections that each correspond to a period of one minute. Time segments for which the alternans ratio is greater than or equal to a threshold value are indicated by dark gray shading 935. In report 900, the threshold equals three.

Time segments for which values of the reference signals are within ranges that have been determined to be acceptable are indicated by a black line 940 along the horizontal axis. The black line indicates that the time segments are free of artifacts that would prevent the alternans measures corresponding to the time segments from being representative of actual alternans.

Report 900 also includes a number of reference signals. Starting at the top of the report, the first reference signal is the heart rate 945 in beats per minute. Measures of both the mean heart rate 950 and the instantaneous heart rate 955 are provided. It is known that alternans may be detected more easily when the heart rate is elevated. Accordingly, inclusion of the heart rate permits an operator to determine whether high levels of alternans have occurred in periods in which they would be expected.

Next, report 900 includes a measure 960 of the percentage of bad beats (i.e., beats that are more than 10% premature or beats having shapes that differ from the shape of a normal beat by more than 10%). Periods for which more than a predetermined percentage of the beats are bad are indicated by light gray shading. In report 900, the predetermined percentage is 10%. Black lines are not displayed along the horizontal axes of the alternans measurements for periods in which the percentage of bad beats exceeds the predetermined percentage.

Report 900 next includes a measure 965 of the noise in the eVM lead. Noise levels above a threshold level are indicated by light gray shading. High noise may obscure alternans and results in a false negative determination.

The noise measure 965 is followed by the alternans measurements 910–930. After the alternans measurements, report 900 includes the rate of exercise 970. When a bicycle is used to perform exercise, the rate of exercise 970 is displayed in rotations per minute relative to the heart rate. Repetitive movement at one half of the heart rate can result in a peak in the signal power spectrum that may mimic alternans. Accordingly, an exercise rate that differs from ⅓ or ⅔ of the heart rate by 7% (i.e., does not fall in the ranges from 26% to 40% or from 60% to 74% of the heart rate) for 8% or more of the beats in any group of 128 beats (and does not equal zero) is shaded in light gray. Black lines are not displayed along the horizontal axes of the alternans measurements for periods in which the exercise measure is shaded gray.

Report 900 next displays a measure 975 of respiration. The respiration measure 975 indicates the presence and amplitude of a peak in the respiration waveform at 0.25 cycles per beat. The respiration measure 975 is expressed using $P_{0.25}$, as discussed above. In other reports, the respiration measure 975 may be expressed using $P_{0.25}'$ or any other measure of dynamic properties of the respiratory activity or of the relationship between respiratory activity and the ECG signal. Periods for which the amplitude of the peak exceeds a threshold value are indicated by light gray shading. Black lines are not displayed along the horizontal axes of the alternans measurements for periods in which the respiration measure is shaded gray.

Finally, report 900 includes a reference signal referred to as HR Delta 980. HR Delta 980 corresponds to the difference between the highest and lowest instantaneous heart rates in a 128 beat interval. Rapidly varying heart rates can result in false alternans measurements. Accordingly, the HR Delta measure is shaded gray for periods in which HR Delta exceeds a threshold level. Black lines are not displayed along the horizontal axes of the alternans measurements for periods in which HR Delta is shaded gray.

Other measures of heart rate variability also could be used. For example, it has been found that a low frequency fluctuation in the heart rate tends to break up a pattern of alternans and increase the difficulty of detecting alternans.

Report 900 also identifies stages of the protocol for which the alternans measurements are generated. The stages are identified by labels 985 and corresponding dashed vertical lines 990. The protocol illustrated in report 900 begins with the patient in a supine position, as indicated by the label "Supine". After eight minutes, the patient begins pedalling a bike, as indicated by the "Sitting Exercise" label. At about eleven minutes and ten seconds into the protocol, the patient's level of exercise increases. This is indicated by the stage "2" label. Finally, at about thirteen and a quarter minutes into the protocol, the patient begins a recovery period. This is indicated by the "recovery" label.

Report 900 also includes information corresponding to a segment (i.e., a group of 128 beats) that was automatically identified by processor 105 as satisfying a set of selection requirements. The segment is indicated by a vertical line 995 and, in report 900, occurs at twelve minutes and four seconds into the protocol. Three numbers 997 are provided at the upper left corner of each alternans measurement. These numbers correspond, respectively, to the alternans voltage, the alternans ratio, and the alternans noise level for the selected segment.

Figure 10:
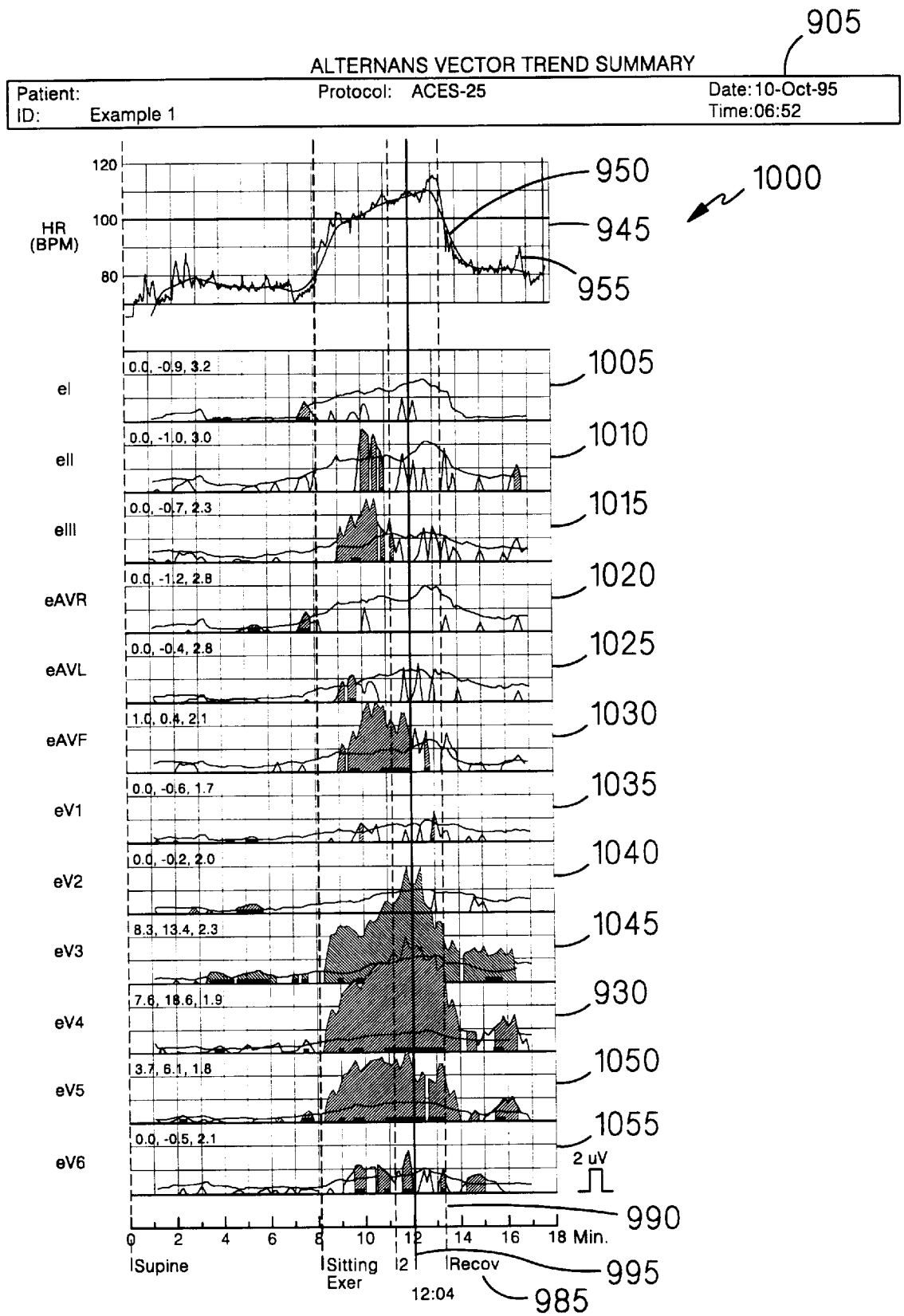

FIG. 10 illustrates a trend report 1000 that is an alternative to trend report 900. Like report 900, report 1000 includes an informational segment 905 that identifies the title of the report ("Alternans 12 Lead Trend Summary") and other information. Report 1000 also includes alternans measurement eV4 930 and a measure of the heart rate 945, including the mean heart rate 950 and the instantaneous heart rate 955. Report 1000 also identifies the stages of the protocol using labels 985 and corresponding dashed vertical lines 990, and displays information corresponding to the processor-selected segment identified by vertical line 995.

Report 1000 differs from report 900 in that, instead of the additional alternans measurements (i.e., eVM, eX, eY and eZ) and reference signals (i.e., % Bad, Noise, RPM, Resp and HR Delta) included in report 900, report 1000 includes alternans measurements for eleven additional leads. These leads are represented by the signals eI 1005, eII 1010, eIII 1015, eAVR 1020, eAVL 1025, eAVF 1030, eV1 1035, eV2 1040, eV3 1045, eV5 1050 and eV6 1055.

Processor 105 also may generate other types of reports. For example, processor 105 may generate the spectrum report 1100 illustrated in FIG. 11. Report 1100, entitled "Alternans Vector Spectrum Report", is produced for the segment automatically selected by processor 105 and identified by vertical line 995 in FIG. 9 or for a user-selected segment.

Report 1100 includes a patient information section 1105 that provides information about the patient. Report 1100 also includes a test detail section 1110. This section identifies the protocol, the position of the selected segment within the protocol, and properties of the reference signals for the selected segment.

Next, report 1100 provides numerical test results 1115 at the selected segment. In addition to the numerical test results, report 1100 provides a frequency power spectrum 1120, in cycles per beat, for each of the five alternans measurements. Report 11 also provides a frequency power spectrum 1125 for RR, the interval between the R points of successive beats. Since RR corresponds to the heart rate, the power spectrum of RR also corresponds to the heart rate.

Figure 12:
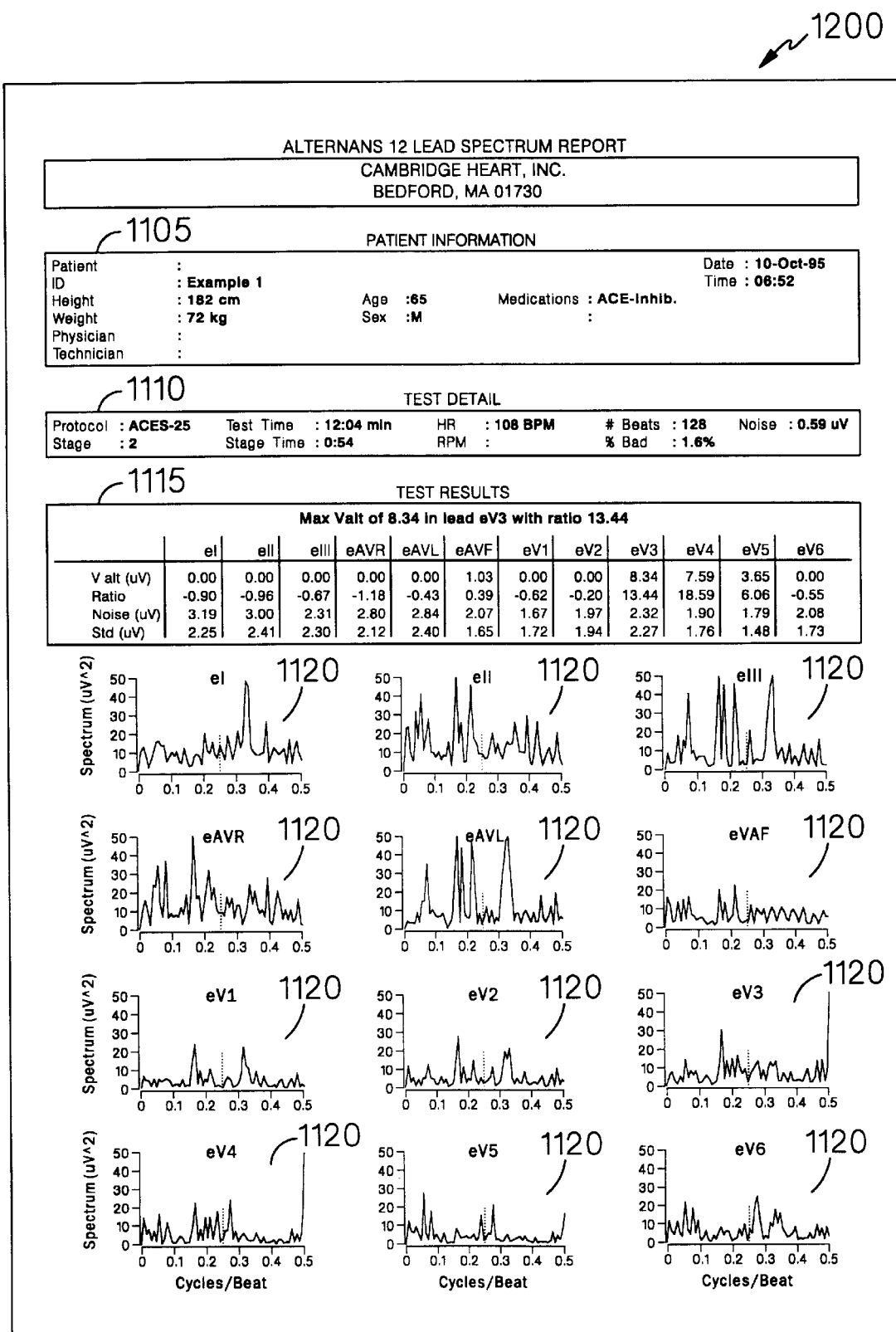

Processor 105 also may produce the spectrum report 1200 illustrated in FIG. 12. This report, entitled "Alternans 12 Lead Spectrum Report", provides the same information as the spectrum report 1100. However, instead of providing information corresponding to the alternans measurements provided in trend report 900, report 1200 provides information corresponding to the alternans measurements provided in trend report 1000.

Other embodiments are within the scope of the following claims.

What is claimed is:

1. A method of permitting assessment of cardiac electrical stability, comprising:

generating an alternans measure using a physiologic signal representative of activity of a patient's heart;

generating a reference signal that provides information as to whether the alternans measure is representative of cardiac electrical stability; and visually presenting the alternans measure and the reference signal in a way that permits visual evaluation of whether the alternans measure is representative of cardiac electrical stability in view of characteristics of the reference signal.

2. The method of claim 1, wherein the step of visually presenting comprises graphically displaying the alternans measure and the reference signal.

3. The method of claim 2, wherein the step of visually presenting comprises displaying the alternans measure and the reference signal using a common time axis.

4. The method of claim 3, wherein the step of visually presenting comprises marking portions of the common time axis, the marked portions of the common time axis corresponding to time segments in which the alternans measure is expected to be more representative of cardiac electrical stability than time segments to which unmarked portions of the common time axis correspond.

5. The method of claim 4, wherein the step of visually presenting comprises shading portions of the graphically displayed alternans measure.

6. The method of claim 1, wherein the reference signal is indicative of a parameter that affects reliability of the alternans measure.

7. The method of claim 6, wherein the parameter masks the presence of alternans.

8. The method of claim 6, wherein the parameter mimics the presence of alternans.

9. The method of claim 1, wherein the reference signal is indicative of a parameter that affects generation of alternans.

10. The method of claim 1, wherein the reference signal comprises a measure of the patient's heart rate.

11. The method of claim 10, wherein the reference signal comprises a measure of mean values of the patient's heart rate at different times.

12. The method of claim 10, wherein the reference signal comprises a measure of instantaneous values of the patient's heart rate at different times.

13. The method of claim 10, wherein the reference signal comprises a measure of variations in the patient's heart rate.

14. The method of claim 1, wherein the reference signal comprises a measure of defects in the physiologic signal.

15. The method of claim 14, wherein the physiologic signal comprises a sequence of ECG beats and wherein the reference signal comprises a measure of a number of ectopic beats in the sequence at different times.

16. The method of claim 1, wherein the reference signal comprises a measure of noise in the physiologic signal.

17. The method of claim 16, wherein the reference signal comprises a measure of noise in a frequency band of the physiologic signal.

18. The method of claim 17, wherein bounds of the frequency band vary over time and are related to the patient's heart rate at different times.

19. The method of claim 16, wherein the reference signal comprises a measure of levels of noise in the physiologic signal relative to amplitudes of the physiologic signal at different times.

20. The method of claim 1, wherein the reference signal comprises a measure of the patient's respiratory activity.

21. The method of claim 1, wherein the reference signal comprises a measure of exercise by the patient.

22. The method of claim 1, wherein the reference signal comprises a measure of the presence of ischemia in the patient's heart.

23. The method of claim 1, wherein the reference signal comprises a measure of variations in ST segments of beats of an ECG signal of the patient.

24. The method of claim 1, wherein the reference signal comprises a measure of one or more QT intervals of an ECG signal of the patient.

25. The method of claim 24, wherein the reference signal comprises a measure of dispersion of QT intervals in beats of the ECG signal.

26. A method of permitting assessment of cardiac electrical stability, comprising:

sensing an ECG signal representative of activity of a patient's heart;

processing the ECG signal to generate a measure of cardiac electrical stability;

generating a reference signal that provides information as to whether the measure is representative of cardiac electrical stability; and visually presenting the measure and the reference signal at common times in a way that permits visual evaluation of whether the measure is representative of cardiac electrical stability in view of characteristics of the reference signal.

27. The method of claim 26, wherein the measure of cardiac electrical stability comprises an alternans measure, and the reference signal provides information as to whether the alternans measure is representative of cardiac electrical stability.

28. The method of claim 26, wherein the measure of cardiac electrical stability comprises a measure involving one or more QT intervals of the ECG signal.

29. The method of claim 28, wherein the measure of cardiac electrical stability comprises a measure of dispersion of QT intervals in beats of the ECG signal.

30. A system for permitting assessment of cardiac electrical stability, comprising:

means for generating an alternans measure using a physiologic signal representative of activity of a patient's heart;

means for generating a reference signal that provides information as to whether the alternans measure is representative of cardiac electrical stability; and means for visually presenting the alternans measure and the reference signal in a way that permits visual evaluation of whether the alternans measure is representative of cardiac electrical stability in view of characteristics of the reference signal.

31. Computer software, residing on a computer-readable storage medium, for use in a computer system for permitting assessment of cardiac electrical stability, the software comprising instructions for causing the computer system to:

generate an alternans measure using a physiologic signal representative of activity of a patient's heart;

generate a reference signal that provides information as to whether the alternans measure is representative of cardiac electrical stability; and visually present the alternans measure and the reference signal in a way that permits visual evaluation of whether the alternans measure is representative of cardiac electrical stability in view of characteristics of the reference signal.

* * * * *